United States Patent
Baumgartner et al.

(10) Patent No.: US 8,353,916 B2
(45) Date of Patent: Jan. 15, 2013

(54) QUICK-RELEASE GUIDE ASSEMBLY FOR ELEMENTS OF OR FOR AN EXTERNAL FIXATION SYSTEM

(75) Inventors: Thomas Baumgartner, Derendingen (CH); Andreas Bernhard, Meinisberg (CH)

(73) Assignee: Stryker Trauma S.A. (CH)

( * ) Notice: Subject to any disclaimer, the term of this patent is extended or adjusted under 35 U.S.C. 154(b) by 1487 days.

(21) Appl. No.: 11/439,569

(22) Filed: May 23, 2006

(65) Prior Publication Data
US 2006/0293688 A1    Dec. 28, 2006

(30) Foreign Application Priority Data
Jun. 1, 2005 (EP) .................................... 05104737

(51) Int. Cl.
*A61B 17/90* (2006.01)
*A61B 17/56* (2006.01)

(52) U.S. Cl. ........................................ 606/96; 606/86 R

(58) Field of Classification Search ............... 606/86 R, 606/87, 96–99, 104, 88, 89, 71, 282, 86 B; 408/241 G, 97, 115 R, 115 B; 24/629, 633, 24/639, 640, 642, 656; 403/229, 359.3, 321–330
See application file for complete search history.

(56) References Cited

U.S. PATENT DOCUMENTS

| | | | | |
|---|---|---|---|---|
| 4,528,980 A * | 7/1985 | Kenna | ............................. | 606/80 |
| 4,651,724 A * | 3/1987 | Berentey et al. | ............... | 606/284 |
| 5,257,558 A * | 11/1993 | Farzin-Nia et al. | ............. | 81/418 |
| 5,851,207 A | 12/1998 | Cesarone | | |
| 5,938,686 A * | 8/1999 | Benderev et al. | ............. | 606/232 |
| 2004/0255439 A1* | 12/2004 | Benedict | ......................... | 24/640 |
| 2005/0038444 A1 | 2/2005 | Binder et al. | | |
| 2005/0137606 A1 | 6/2005 | Binder et al. | | |

FOREIGN PATENT DOCUMENTS
EP    229676    7/1987
EP    780092    6/1997

OTHER PUBLICATIONS
European Search Report, Nov. 9, 2005.

\* cited by examiner

*Primary Examiner* — Thomas Barrett
*Assistant Examiner* — Michael T Schaper
(74) *Attorney, Agent, or Firm* — Lerner, David, Littenberg, Krumholz & Mentlik, LLP

(57) ABSTRACT

A quick-release guide assembly for an external fixation system has a body with at least one hole and a handle portion with a handle bar. The device body comprises at least one extension having a first coupling portion. The handle comprises a complementary second coupling portion, wherein one coupling portion comprising a spring actuated locking pin, wherein an actuator knob is provided to release the locking pin. Therefore the coupling portion of the handle can be releasably attached to the guide body, enabling a quick change of device bodies having different oriented and arranged holes.

21 Claims, 6 Drawing Sheets

400
QUICK-RELEASE GUIDE ASSEMBLY FOR ELEMENTS OF OR FOR AN EXTERNAL FIXATION SYSTEM

CROSS-REFERENCE TO RELATED APPLICATIONS

The present application claims priority from European Patent Application No. EP 05 104 737.1 filed on Jun. 1, 2005, the disclosure of which is hereby incorporated by reference herein.

BACKGROUND OF THE INVENTION

The invention relates to a quick-release guide assembly for elements of or used for an external fixation system.

The use of surgical fixation systems for a variety of orthopedic applications is widely accepted. Plates are used by surgeons to stabilize or align a patient's bone as well as alter compression of patient's bones. Such plates are then fastened to the bones with a plurality of fasteners such as screws that are installed through holes in the plate. However beside plates such elements to be guided are e.g. drills, taps, screws, pins, other fasteners or instruments.

Each fixation pin should properly align with its associated pin clamp hole so that each pin is seated correctly with the external fixation system and enters the bone at an appropriate angle. Any misalignment of the pin within the pin clamp hole may result in an unstable or insecure connection of the external fixation system, e.g. a plate, to the bone, thus potentially defeating the usefulness of the external fixation system.

It is known in the field to use drill guides to improve the quality and accurateness of the drilled bores in view of the external fixation system to be used. Such a drill guide is known from U.S. Publication 20050038444 and 20050137606.

Another drill guide is known from U.S. Pat. No. 4,528,980. The drill guide is manipulated through use of a handle which is releasably connected to the drill structure for manipulating the shell.

The handle structure includes a tip end portion constructed and arranged to releasably fit within either one of the bushings comprising the drill guide structure. Each bushing includes an open-ended slot, and a key on the outside of the tip end portion of the handle structure mates within the slot when the handle is fitted into one of the bushings. This overall structural relationship properly positions the handle structure relative to the drill guide and additionally prevents relative rotation.

This known device has the drawback that one of the holes on the surface of the drill guide plate is used to hold the handle and cannot be chosen for drilling a hole. Furthermore, the proximal end of the handle has an axis substantially perpendicular to the plane of the drill guide structure and may be inconvenient for the surgeon to use a drill in this environment.

Furthermore, hospitals are often interested in providing one single handle for different applications to be able to gain room in a sterilization box and reduce costs. Surgeons are interested in using guide assemblies wherein elements can be connected more flexibly to follow the space requirements within the framework of a chirurgical intervention and to optimize the handling for the user.

SUMMARY OF THE INVENTION

Based on this prior art it is one aspect of the invention to provide an improved handle drill guide with a releasable handle.

For this purpose, according to the invention, the drill guide has the features of a quick-release guide assembly for elements of, or used for, an external fixation system. The assembly comprising a body with at least one hole, a handle portion with a handle bar and a connecting portion, which can be releasably attached to the body. The body comprises at least one appendage having a first connecting portion, in that the handle comprises a complementary second connecting portion, one connecting portion comprising a spring actuated locking pin. An actuator knob is provided to release the locking pin. The appendage is inclined to point away from the underside of the body. The underside of the appendage is flush with the underside of the device body. The body may comprise one, two, three or four appendages on the different sides of the body, preferably mounted in the middle of each side of the body. The first connecting portion comprises a hook and second connecting portion comprises a slit adapted to receive the hook. The hook is mounted, preferably in one piece with a bar, in a way that the prolongation of the underside of the hook crosses the underside of the body at the median line of the body. The hook comprises a nose portion and an opposing web defining a tapering slit opening behind the nose into a locking slit. A second connecting portion comprises a pin oriented perpendicular to the hook receiving slit, wherein a guiding slit is provided in the plane comprising the pin and perpendicular to the plane of the receiving slit to enable a transverse movement of the pin in the guiding slit. A bore is provided parallel to the hook receiving slit and centered within the width of the guiding slit to accommodate, on the other side towards the mouth of the bore, an actuator knob, having a bore to encompass the pin, and, on the side towards the end of the bore, a spring to push the pin in his idle position against the wall of the guiding slit near the actuator knob. The guide assembly may be a drill guide assembly and the elements of the external fixation system are from the group encompassing a drill, a tap, a screw, a pin, fixation elements, or instruments.

BRIEF DESCRIPTION OF THE DRAWINGS

The invention will be explained in greater detail by means of a description of exemplary embodiments, with reference to a drawing containing the following figures.

DETAILED DESCRIPTION

Features and advantages of the present invention in addition to those mentioned above will become apparent to those skilled in the art from a reading of the following detailed description.

Figure 1:
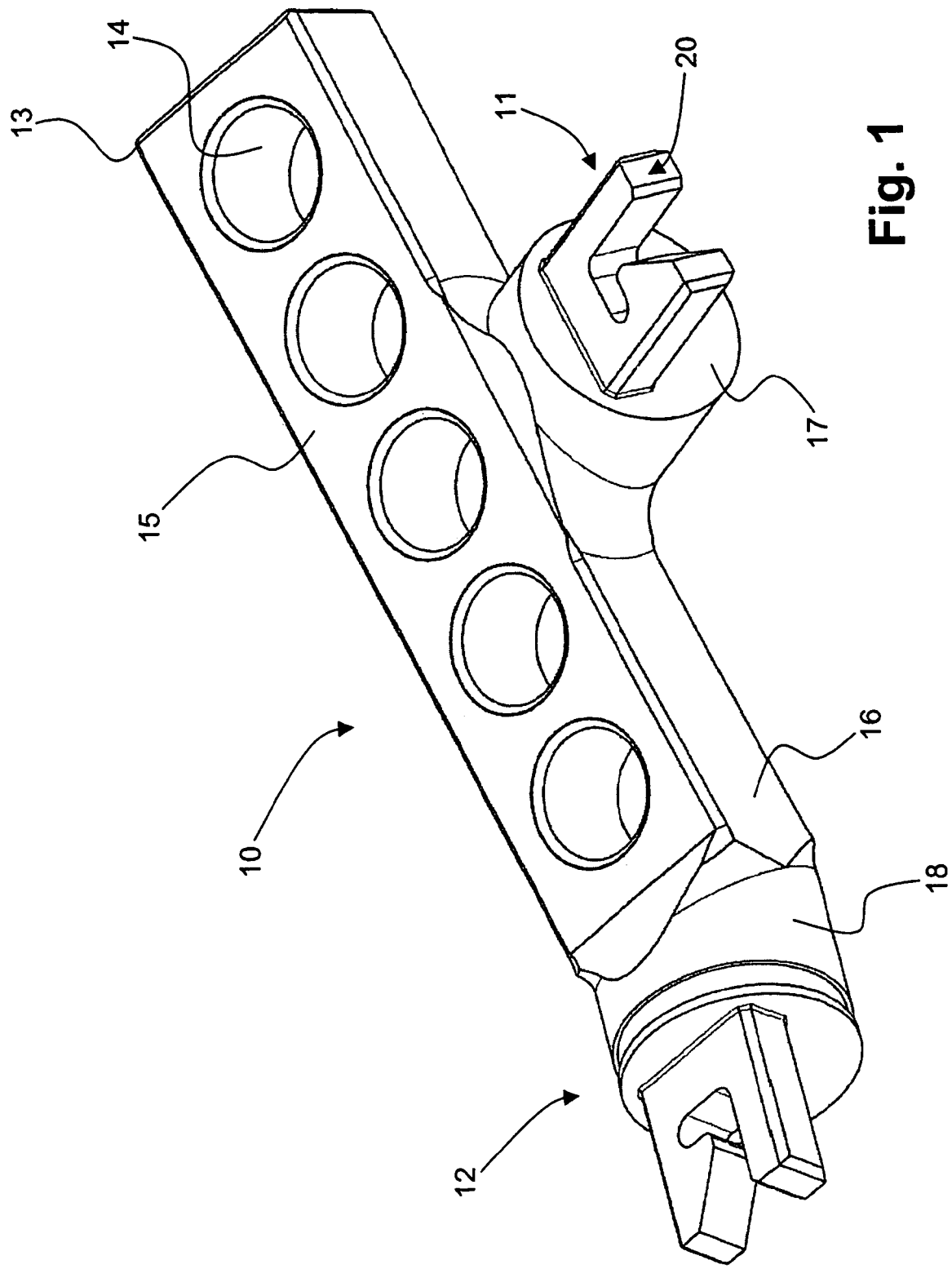
FIG. 1 is a perspective view of a drill guide without handle including a pair of hooks according to one embodiment of the invention.

Referring to FIG. 1, there is shown a preferred drill guide 10 having two coupling appendages 11 and 12. The drill guide 10 comprises a body 13 being fitted with five through holes 14. In the preferred embodiment body 13 is e.g. a rectangular parallelepiped with the holes 14 oriented in one row. The number, location and orientation of holes 14 depend from the specific application of the drill guide. The holes 14 of drill guide 10 are oriented perpendicular or inclined to the surface 15 of body 13 and in the preferred embodiment are internally threaded. Surface 15 is per definition the upper surface of the drill guide 10, i.e. the surface opposite to the bone of the patient to be treated.

Two coupling appendages 11 and 12 are attached to body 10. The first appendage 11 is attached to a side surface 16 in the middle of the longer side of the drill guide 10. The second appendage 12 is attached to one of the shorter side surfaces of the drill guide 10. In other embodiments there may be provided only one or three or even four coupling appendages on different sides or on every side surface of the body 13.

Each appendage 11 or 12 comprises an intermediate bar section 18 with an abutment surface 17 on which is provided a hook 20. In the preferred embodiment the main axis of the bar section 18 is inclined compared to the upper surface 15 of the body 10. The inclination is such that the abutment surface 17 and the hook 20 are oriented away from the underside 19 (see FIG. 3) of drill guide body 13, i.e. the side opposite to the surface 15 and upwardly of surface 15.

Figure 2:
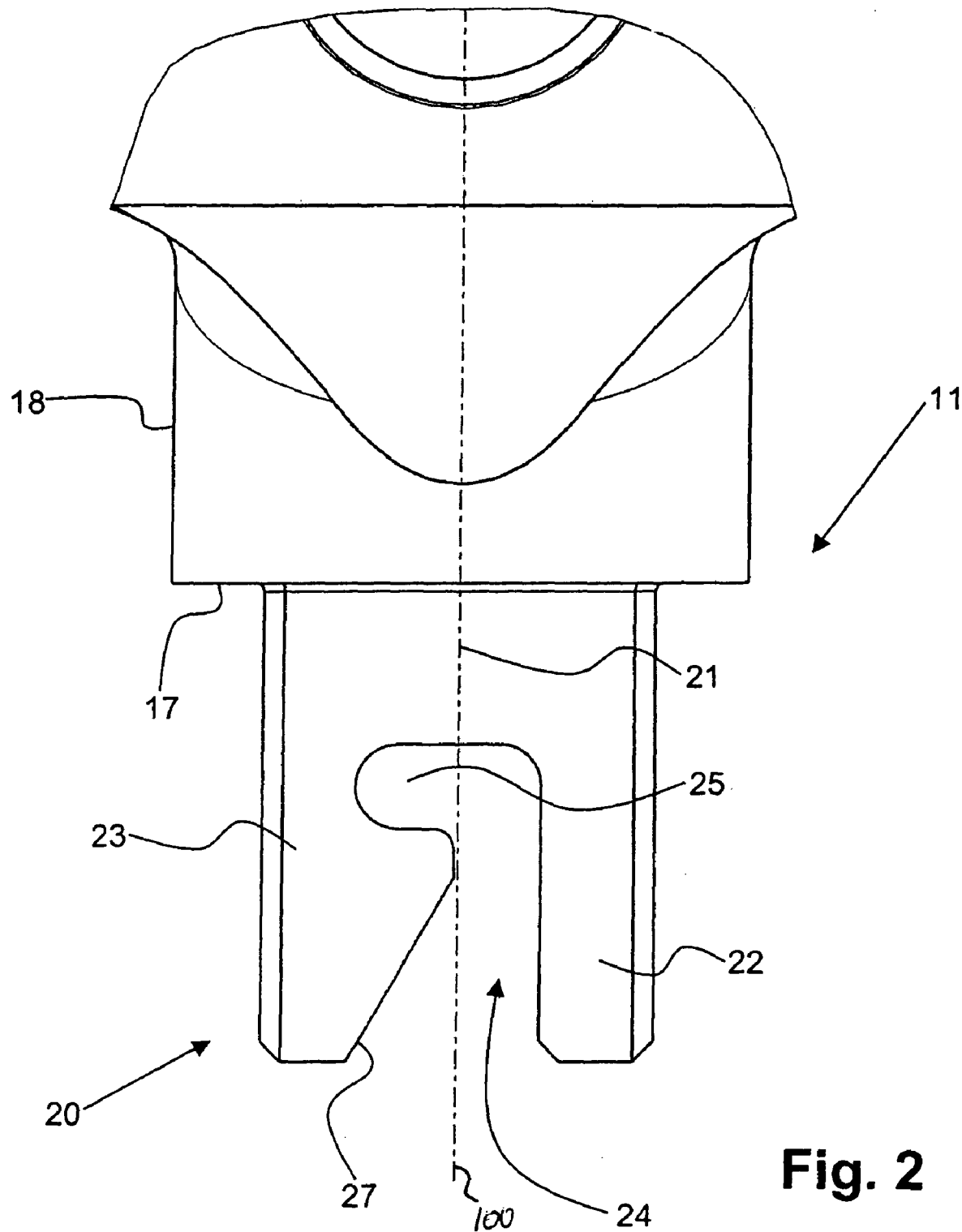
FIG. 2 is a plan view of a hooked end of the drill guide of FIG. 1.

FIG. 2 shows a plan view on one of the hooks 20 of the drill guide 10 of FIG. 1. Note that the same features receive, in all Figs., the same reference numerals. The body of hook 20 comprises an engagement section 21 adjacent section 18, extending on one side into a counter web 22 with the form of a parallelepiped or pin which may be round, and on the other in a nose 23. The web 22 is provided opposite to the retaining nose 23 having the same length over the abutment surface 17. Between the nose 23 and the web 22 there is a tapering slit surface 24, opening internally on the nose 23 into a transverse oriented locking slot 25. The inclination of the most preferred tapering angle of surface 24 is 30 degrees but can also be chosen preferably between 5 and 60 degrees. The length of nose 23 and web 22 are such that the slit 24 starts at the free end of nose 23 and web 22 with a width of e.g. more than 4.5 millimeter, narrowing towards approximately 2 millimeter, i.e. less than a half of the initial spacing; wherein the locking slot 25 has a width perpendicular to axis 100 of approximately 4.5 millimeter and a depth parallel to axis 100 of approximately 2 millimeter. These dimensions are adapted for the handle 30 shown in FIG. 3 to be used in connection with body 13 which in the preferred embodiment has a length of approximately 60 millimeters and a width of approximately 14 millimeters. It is clear that other dimensions of the device can be contemplated. It is preferred that the length of the locking slot 25 along axis 100 is at least the double of the width of said locking slot 25, i.e. a pin 41 to be inserted in said slot 25 can be lodged completely behind the nose 23.

Figure 3:
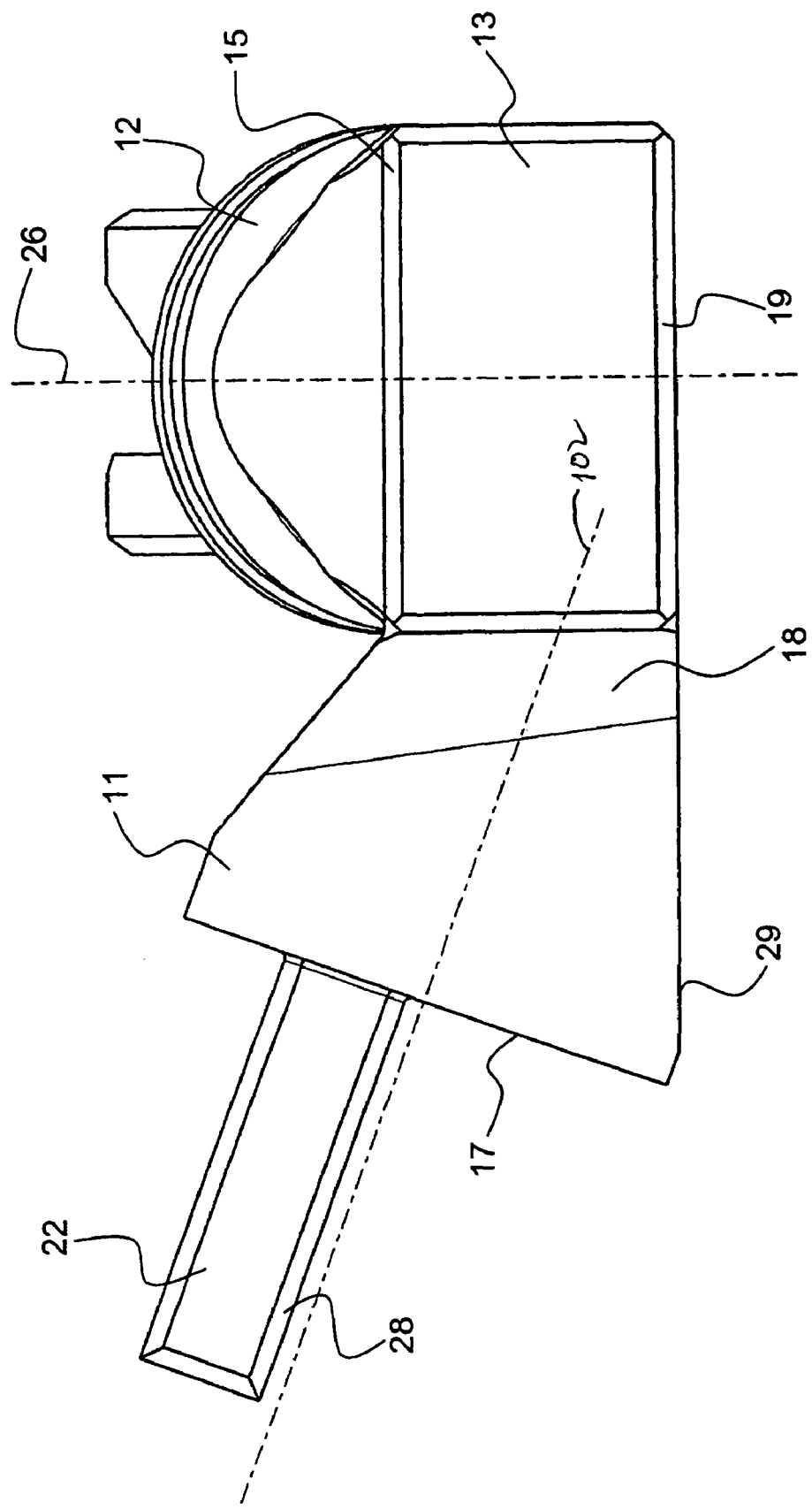
FIG. 3 is a right side view of the drill guide of FIG. 1.

FIG. 3 is a side view of the preferred drill guide 10 from the side surface opposite to appendage 12. It can be seen from FIG. 3 that the underside 19 of the body 13 is extended into the underside 29 of body 18 of appendage 12. This creates a larger underside surface. In other embodiments the intermediary bar 18 can also chosen to be purely cylindrical.

Hook 20 is mounted, preferably in one piece with the bar 18, in such a way that the elongation of the underside 28 of web 22 or nose 23 crosses the underside 19 of the body 13 at the median line 26 of body 13. This brings the hook 20 in an eccentric position on the abutment surface 17. Thus the body of hook 20 is offset towards surface 15 of body 10.

Figure 4:
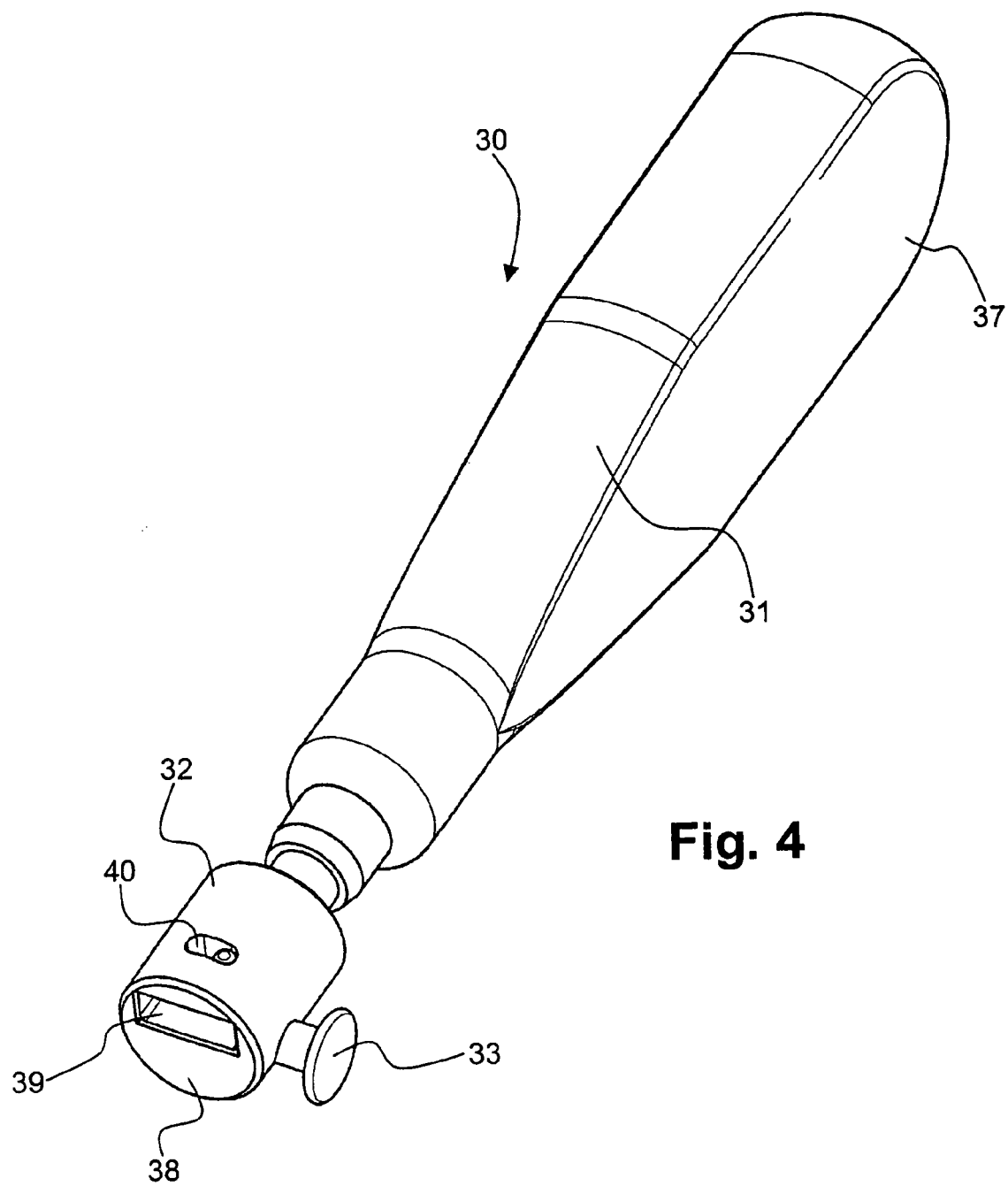
FIG. 4 is a perspective view of a handle for use with the hooked portion of the drill guide according to FIG. 1.

FIG. 4 is a perspective view of a handle 30 of the drill guide 10 according to FIG. 1. The handle 30 comprises a handle bar 31 and a sleeve end portion 32. The two portions 31 and 32 may be provided in one piece but the handle bar 31 can be mounted on an extension shaft of the end portion 32.

Figure 5:
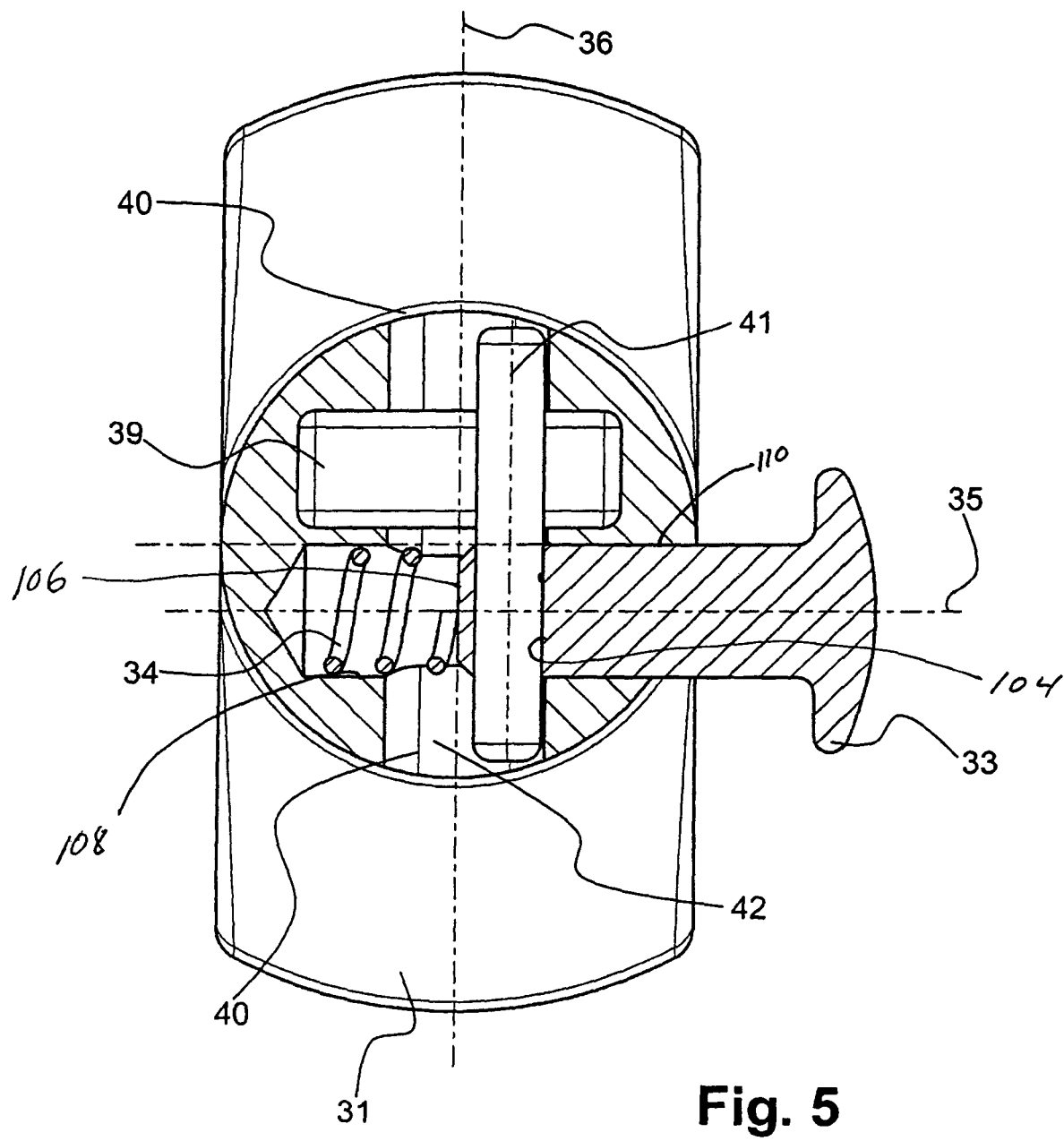
FIG. 5 is a cross-sectional view of a coupling sleeve of the handle of FIG. 4.

The sleeve portion 32 comprises an actuator knob 33 which can be pushed against the action of a spring 34 shown in FIG. 5. The movement of actuator knob 33 is possible along an axis 35 perpendicular to the central longitudinal axis 36 of the handle bar 31. It can be seen from FIG. 4 that handle bar 31 is flattened on opposite sides 37 and that the actuator surface of knob 33 is mainly oriented to the plane of the flattened side surfaces 37, e.g. parallel.

The sleeve end portion 32 ends opposite to the handle bar 31 in an abutment surface 38. Abutment surface 38 is provided to abut against surface 17 of intermediary bar 18. The sleeve end portion 32 comprises a rectangular slot 39 provided to receive hook 20 of the drill guide 10. As mentioned in connection with FIG. 3, hook 20 is eccentric to the axis 102 of intermediary bar 18 as is slot 39 with respect to axis 36.

The sleeve end portion 32 furthermore comprises two open inspection slits 40 (on opposite sides of sleeve 32) within which one and the same perpendicular oriented pin 41 can be seen. These features disclosing the operation of knob 33 are better shown in FIG. 5.

FIG. 5 is a cross-section view of sleeve 32 of the handle 30. The main axis 35 of a guiding bore 110 and knob 33 mounted therein is located below the slit 39. The bottom of knob 33 comprises a transverse bore 104 to accommodate the locking pin 41. The end surface 106 of the knob 33 pushes against a spring 34, supported on the other side against the bottom 108 of guiding bore 110 along axis 35. The locking pin 41 within the bore 104 of the knob 33 prevents knob 33 from being pushed out of guiding bore 110. The bore comprising the spring 34 can be greater than the width of a guiding slit 42 which receives pin 41, although the bottom 108 of the guiding bore 110 usually provides enough guiding force for the spring 34. Additionally the bottom of the knob can be formed as a cone to guide the end helix of the spring 34.

Between the two opposite open inspection slits 40 is provided a through-going guiding slit 42 receiving the locking pin 41. Therefore a portion of the locking pin 41 is always blocking the slit 39. In this context locking pin 41 has a distance from front surface 38 of the handle 30 and locking slit 25 has a distance from abutment surface 17 of appendage 11 or 12 so that, upon contact of the two abutment surfaces 38 and 17, pin 41 engages into the locking slit 25.

When handle 30 is positioned on the appendage 11 or 12 so that the abutment surfaces 17 and 38 are brought together, pin 41 glides within the guiding slit 42 from the idle position, shown in FIG. 5, where it is located opposite to nose 23, over the inclined surface 27 against the force of the spring 34 until pin 41 snaps back within the locking slot 25. The drill guide 10 with attached handle 30 is then usable by a surgeon. When the drill guide has to be changed or switched, then the surgeon activates the knob 33 and separates handle 30 from the drill guide body 13 through bringing the pin 41 against the force of the spring 34 in the locking slot 25 in a position to be liberated.

Figure 6:
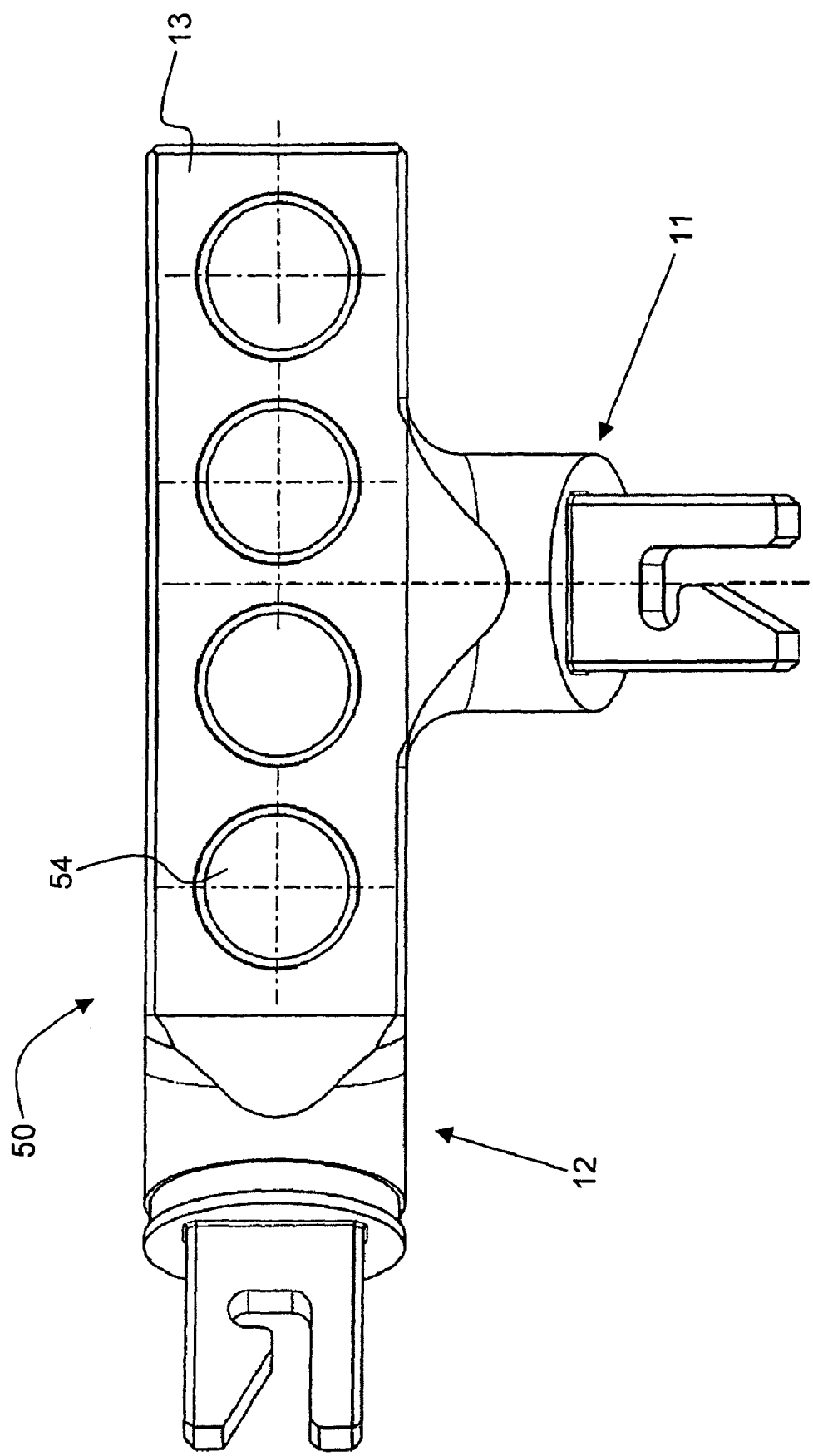
FIG. 6 is a plan view of a drill guide without handle according to another embodiment of the invention.

FIG. 6 is plan view of a drill guide 50 without handle 30 according to another embodiment of the invention. The drill guide 50 comprises a drill guide body 13 being shorter than the body of drill guide 10. There are four holes 54 in two groups of two holes 54. The two appendages 11 and 12 allow attaching a handle 30 on the longer or shorter side of the body 13. In other embodiments there may be inclined holes or holes of different diameter. The holes can be through going bores with smooth surfaces or they can be threaded over a portion or completely.

Although the description of the drawings always mention a drill guide, it is clear, that such a quick-release guide assembly can also be used for other elements of or used for an external fixation system. These parts can be taps, screws, pins or other fastener elements. The external fixation system can comprise a plate of other elements for which the guide can be used for.

Handle 30 is preferably made in aluminum, stainless steel, plastic or titanium. The same applies to items with the reference numerals 31 to 41 beside the coil spring 34, preferably made in stainless steel. The drill guide 10 is preferably made in aluminum, stainless steel, plastic or titanium or alternatively in PEEK (polyether ether ketones) to obtain X ray transparency or carbon fibers.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A quick-release guide assembly for elements for an external fixation system, comprising:
   a device body having a planar portion with a plurality of holes therethrough, the device body planar portion having a pair of opposite shorter side surfaces and a pair of opposite longer side surfaces, connecting the opposite shorter side surfaces, the pair of opposite shorter side surfaces being shorter than the pair of opposite longer side surfaces, at least one shorter side surface and at least one longer side surface each having a connecting element extending outwardly from the device body at an acute angle to the body planar portion, and
   a handle portion with a handle bar and a connecting element, which handle portion connecting element can be releasably attached to each connecting element on the shorter and longer side surface, the handle portion connecting element comprising a spring actuated locking pin, wherein an actuator knob is provided to release the locking pin wherein the device body has a bottom surface and a top surface each connecting the two shorter and two longer side surfaces wherein each connecting element on the shorter and longer side surfaces is inclined to point away from the bottom surface of the device body planar portion toward the top surface thereof.

2. The guide assembly according to claim 1, wherein each connecting element on the shorter and longer side surface has a surface which is flush with the bottom surface of the device body planar portion.

3. The guide assembly according to claim 1, comprising at least three connecting elements respectively located on three different side surfaces of the pair of longer and the pair of shorter side surfaces of the device body planar portion.

4. The guide assembly according to claim 1, wherein each connecting element on the longer and shorter side surface comprises a hook and the handle portion connecting element comprises a hook receiving slit.

5. The guide assembly according to claim 4, wherein the hook and the handle bar are one piece, the hook being mounted in a way that the prolongation of an underside of the hook crosses the bottom surface of the device body planar portion at a median line of a longer or shorter side surface of the device body.

6. The guide assembly according to claim 4, wherein the hook comprises a nose portion and an opposing web defining a tapering slit, opening behind the nose into a locking slit.

7. The guide assembly according to claim 6, wherein the connecting element on the handle portion comprises a pin oriented perpendicular to the hook receiving slit, wherein a guiding slit is provided in a plane comprising the pin and perpendicular to a plane of the hook receiving slit to enable a transverse movement of the pin in the guiding slit, wherein a first bore is provided parallel to the hook receiving slit and centered within a width of the guiding slit to accommodate, on the side towards a mouth of the bore, the actuator knob, having a second bore to encompass the pin, and, on a side towards an end of the first bore opposite the mouth, a spring to push the pin against a wall of the guiding slit nearest the actuator knob.

8. The guide assembly according to claim 1, wherein the guide assembly is a drill guide assembly and the elements for the external fixation system are selected from the group consisting of a drill, a tap, a screw, a pin, fixation elements, or instruments.

9. A method of attaching elements of an external fixation system using a quick-release guide assembly according to claim 1 comprising:
   providing the device body with the plurality of holes for an element of the external fixation system, and
   providing the handle portion with the handle bar and the connecting element therein comprising the actuator knob, releasably attaching the handle portion connecting element to the device body longer and shorter side surfaces having the connecting elements thereon, wherein the connecting element on the handle portion comprises the spring actuated locking pin, wherein the actuator knob is pushed to release the locking pin to separate the device body from the handle portion while maintained in a hand.

10. A quick release guide assembly comprising:
    a planar guide body having a bone facing surface and an opposite upper surface and first side surface and second side surface connecting the upper and bone contacting surfaces, the first side surface being longer than the second side surface, the first and second side surfaces extending respectively along a first and second central axis respectively, said axes being in non-parallel relationship, said guide body having a plurality of axially aligned guide bores extending from the upper surface to the bone facing surface;
    first and second connecting elements respectively extending from said first and second side surfaces of said guide body, the first and second connecting elements inclined towards the upper surface; and
    a handle having a coupling element for engaging either of said first and second connecting elements on said guide body;
    wherein the coupling element has a first connecting portion comprising a flat hook portion formed by an open passageway and a locking slot extending transverse to the passageway.

11. The guide assembly according to claim 10, wherein the flat hook portion is integrally mounted on the guide body as an extension thereof with the hook crossing the bone contacting surface of the guide body at a median line of a side surface of the body.

12. The guide assembly according to claim 10, wherein the flat hook portion comprises a nose portion and an opposing web defining a tapering passageway, opening behind the nose into the locking slot.

13. A quick release drill guide assembly for elements for an external fixation system comprising:
   a device body having a planar portion with a plurality of holes therethrough, the device body planar portion having a pair of opposite shorter side surfaces and a pair of opposite longer side surfaces connecting the shorter side surfaces, at least one shorter side surface and at least one longer side surface each having a connecting element extending outwardly from the device body at an acute angle to the planar body portion, and
   a handle portion with a handle bar and a connecting element, which can be releasably attached to the connecting element on one of the longer and shorter side surface,
   the handle portion connecting element comprising a spring actuated locking pin, wherein an actuator knob is provided to release the locking pin, wherein the first connecting element comprises a hook and the second connecting element comprises a slit adapted to receive the hook, wherein the device body has a bottom surface and a top surface each connecting the two shorter and two longer side surfaces wherein each connecting element on the longer and shorter side surface is inclined to point away from the bottom surface of the device body planar portion towards the top surface thereof, wherein each connecting element on the longer and shorter side surface has a surface which has an underside that is flush with the bottom surface of the device body planar portion, and wherein the hook is mounted in a way that the prolongation of an underside of the hook crosses the bottom surface of the device body planar portion at a median line of a longer or shorter side surface of the device body.

14. The guide assembly according to claim 13, comprising at least three connecting elements respectively located on three different longer and shorter side surfaces of the pair of longer and the pair of shorter side surfaces of the device body planar portion.

15. The guide assembly according to claim 13 wherein the hook and the handle bar are one piece.

16. The assembly according to claim 13, wherein the hook comprises a nose portion and an opposing web defining a tapering slit, opening behind the nose into a locking slit.

17. The guide assembly according to claim 16, wherein the connecting element on the handle portion comprises a pin oriented perpendicular to the hook receiving slit, wherein a guiding slit is provided in a plane comprising the pin and perpendicular to a plane of the receiving slit to enable a transverse movement of the pin in the guiding slit, wherein a first bore is provided parallel to the hook receiving slit and centered within the width of the guiding slit to accommodate, on the side towards a mouth of the bore, the actuator knob, having a second bore to encompass the pin, and, on the side towards an end of the first bore opposite the mouth, a spring to push the pin against a wall of the guiding slit nearest the actuator knob.

18. A quick release guide assembly comprising:
   a planar guide body having a bone facing surface and an opposite upper surface and first side surface and second side surface connecting the upper and bone contacting surfaces, the first side surface being longer than the second side surface, the first and second side surfaces extending respectively along a first and second central axis respectively, said axes being in non-parallel relationship, said guide body having a plurality of axially aligned guide bores extending from the upper surface to the bone facing surface;
   first and second connecting elements respectively extending from said first and second side surfaces of said guide body, the first and second connecting elements inclined towards the upper surface, and a handle having a coupling element for engaging either of said first and second connecting elements on said guide body and further comprising third and fourth connecting elements extending from third and fourth side surfaces of the planar device body, the third and fourth side surfaces extending from the upper surface to the bone facing surface and respectively parallel to the first and second side surfaces.

19. The guide assembly according to claim 18, wherein the handle coupling element has a connecting portion comprising a flat hook portion formed by an open passageway and a locking slot extending transverse to the passageway.

20. The guide assembly according to claim 19, wherein the flat hook portion is integrally mounted on the guide body as an extension thereof with the hook crossing the bone contacting surface of the guide body at a median line of a side surface of the body.

21. The guide assembly according to claim 19, wherein the flat hook portion comprises a nose portion and an opposing web defining a tapering passageway, opening behind the nose into the locking slot.

* * * * *